US006905691B1

(12) United States Patent
Chatfield et al.

(10) Patent No.: US 6,905,691 B1
(45) Date of Patent: Jun. 14, 2005

(54) VACCINES CONTAINING ATTENUATED BACTERIA

(75) Inventors: Steven Neville Chatfield, Berkshire (GB); Gordon Dougan, London (GB); Mark Sydenham, London (GB)

(73) Assignee: Celltech Pharma Europe Limited (GB)

( * ) Notice: Subject to any disclaimer, the term of this patent is extended or adjusted under 35 U.S.C. 154(b) by 41 days.

(21) Appl. No.: 09/591,447

(22) Filed: Jun. 9, 2000

Related U.S. Application Data

(63) Continuation of application No. PCT/GB98/03680, filed on Dec. 10, 1998.

(30) Foreign Application Priority Data

Dec. 11, 1997 (GB) ............................................ 9726233

(51) Int. Cl.$^7$ ..................... A66K 39/02; A61K 39/295; A61K 39/10; A61K 39/102; A61K 39/108
(52) U.S. Cl. ..................... 424/200.1; 424/184.1; 424/200.1; 424/234.1; 424/235.1; 424/253.1; 424/256.1; 424/257.1; 424/258.1; 424/259.1; 424/278.1; 435/7.35; 435/7.37; 435/23; 435/24; 435/38; 435/69.1; 435/69.3; 435/320.1; 435/440
(58) Field of Search ..................... 424/93.48, 241.1, 424/253.1, 256.1, 257.1, 258.1, 259.1, 163.1, 164.1, 169.1, 200.1, 202.1, 203.1; 435/7.35, 7.37, 7.6, 92, 23.24, 38, 332; 530/388.2

(56) References Cited

U.S. PATENT DOCUMENTS

| 5,527,529 A | 6/1996 | Dougan et al. |
| 5,804,194 A | 9/1998 | Dougan et al. |

FOREIGN PATENT DOCUMENTS

| EP | 0 322 237 B1 | 6/1989 |
| EP | 0 400 958 A2 A3 | 12/1990 |
| EP | 0 524 205 B1 | 1/1993 |
| WO | WO 92/15689 | 9/1992 |
| WO | WO 94/03615 | 2/1994 |

OTHER PUBLICATIONS

Lazar et al. 1996. J. of Bacteriology. 178(6): 1770–1773.*
Missiakas et al. 1996. Mol. Micro. 21(4): 871–884.*
Rouviere et al. 1996. Genes and Develop. 10: 3170–3182.*
Boslego et al., "Gonorrhea Vaccines," chapter 17 of Cryz, Jr., ed., Vaccines and Immunotherapy, Pergamon Press, New York, 1991, pp. 221–223.

(Continued)

Primary Examiner—Lynette R. F. Smith
Assistant Examiner—J. Hines
(74) Attorney, Agent, or Firm—Popovich, Wiles & O'Connell, P.A.

(57) ABSTRACT

The invention relates to a vaccine comprising a bacterium attenuated by a non-reverting mutation in a gene encoding a protein which promotes folding of extracytoplasmic proteins. Such mutations were initially identified as being useful in vaccines from a bank of randomly inserted, transposon mutants in which attenuation was determined as a reduction in virulence of the organism in the mouse model of infection. Site directed mutation of the gene results in a strain which shows at least 4 logs of attenuation when delivered both orally and intravenously. Animals vaccinated with such a strain are protected against subsequent challenge with the parent wild type strain. Finally, heterologous antigens such as the non-toxic and protective, binding domain from tetanus toxin, fragment C, can be delivered via the mucosal immune system using such strains of bacteria. This results in the induction of a fully protective immune response to subsequent challenge with native tetanus toxin.

27 Claims, 4 Drawing Sheets

OTHER PUBLICATIONS

Ellis, "New Technologies for Making Vaccines," chapter 29 of Plotkin et al., eds., *Vaccines*, W.B. Saunders Company, Philadelphia, 1988, pp. 568–575.

Chatfield et al., "Live Salmonella as Vaccines and Carriers of Foreign Antigenic Determinants," *Vaccine*, 7:495–498 (1989).

Hottenrott et al., "The *Escherichia coli* SlyD is a Metal Ion–regulated Peptidyl–prolyl cis/trans –Isomerase," *J. Biol. Chem.*, 272:15697–15701 (1997).

Kleerebezem et al., "Characterization of an *Escherichia coli* rotA Mutant, Affected in Periplasmic Peptidyl–prolyl cis/trans Isomerase," *Molecular Microbiology*, 18:313–320 (1995).

Lazar et al., "SurA Assists the Folding of *Escherichia coli* Outer Membrane Proteins," *J. Bacteriology*, 178:1770–1773 (1996).

Lazar et al., "Role of the *Escherichia coli* SurA Protein in Stationary–Phase Survival," *J. Bacteriology*, 180:5704–5711 (1998).

Liu et al., "Rearrangements in the Genome of the Bacterium *Salmonella typhi*," *Proc. Nat. Acad. Sci. USA*, 92:1018–1022 (1995).

Missiakas et al., "New Components of Protein Folding in Extracytoplasmic Compartments of *Escherichia coli* SurA, FkpA and Skp/OmpH," *Molecular Microbiology*, 21:871–884 (1996).

Rouviere et al., "SurA, a Periplasmic Protein with Peptidyl–prolyl Isomerase Activity, Participates in the Assembly of Outer Membrane Porins," *Genes Dev.*, 10:3170–3182 (1996).

Rudd et al., "A New Family of Peptidyl–prolyl Isomerase," *Trends in Biochemical Sciences*, 20:12–14 (1995).

Schodel et al., "Salmonellae as Oral Vaccine Carriers," *Dev. Biol. Stand.*, 84:245–253 (1995).

Bacon et al., "The Effects of Biochemical Mutation on the Virulence of *Bacterium typhosum*: The Virulence of Mutants," *Br. J. Exp. Pathol.*, 31:714–724 (1950).

Chatfield et al., "Evaluation of *Salmonella typhimurium* Strains Harbouring Defined Mutations in htrA and aroA in the Murine Salmonellosis Model," *Microbiol. Pathog.*, 12:145–151 (1992).

Chatfield et al., "Use of the nirB Promoter to Direct the Stable Expression of Heterologous Antigens in Salmonella Oral Vaccine Strains: Development of a Single–Dose Oral Tetanus Vaccine," *Bio/Technology*, 10:888–892 (1992).

Chatfield et al., "Construction of a Genetically Defined *Salmonella typhi* Ty2 aroA, aroC Mutant for the Engineering of a Candidate Oral Typhoid–Tetanus Vaccine," *Vaccine*, 10(1):53–60 (1992).

Curtiss III et al., "*Salmonella typhimurium* Deletion Mutants Lacking Adenylate Cyclase and Cyclic AMP Receptor Protein are Avirulent and Immunogenic," *Infect. Immun.*, 55(12):3035–3043 (1987).

Dougan et al., "Construction and Characterization of Vaccine Strains of Salmonella Harboring Mutations in Two Different aro Genes," *J. Inf. Dis.*, 158(6):1329–1335 (1988).

Everest et al., "Expression of LacZ from the htrA, nirB and groE Promoters in a Salmonella Vaccine Strain: Influence of Growth in Mammalian Cells," *FEMS Microbiol. Letts.*, 126:97–101 (1995).

Fairweather et al., "Immunization of Mice Against Tetanus with Fragments of Tetanus Toxin Synthesized in *Escherichia coli*," *Infect. Immun.*, 55(11):2541–2545 (1987).

Fairweather et al., "Oral Vaccination of Mice Against Tetanus by Use of a Live Attenuated Salmonella Carrier," *Infect Immun.*, 58(5):1323–1326 (1990).

Gomaz–Duarte et al., "Expression of Fragment C of Tetanus Toxin Fused to a Carboxyl–Terminal Fragment of Diphtheria Toxin in *Salmonella typhi* CVD 908 Vaccine Strain," *Vaccine*, 13(16):1596–1602 (1995).

Harrison et al., "Role of hns in the Virulence Phenotype of Pathogenic Salmonellae," *Mol. Micro.*, 13(1):133–140 (1994).

Hohmann et al., "Evaluation of a phoPlphoQ–deleted, aroA–deleted Live Oral *Salmonella typhi* Vaccine Strain in Human Volunteers," *Vaccine*, 14(1):19–24 (1996).

Hone et al., "Construction of Defined galE Mutants of Salmonella for Use as Vaccines," *J. Infect. Dis.*, 156(1):167–174 (1987).

Hull et al., "Construction and Expression of Recombinant Plasmids Encoding Type 1 or D–Mannose–Resistant Pili from a Urinary Tract Infection *Escherichia coli* Isolate," *Infect. Immun.*, 33(3):933–938 (1981).

Johnson et al., "The Role of a Stress–Response Protein in *Salmonella typhimurium* Virulence," *Mol. Micro.*, 5(2):401–407 (1991).

Jones et al., "Oral Vaccination of Calves Against Experimental Salmonellosis Using a Double aro Mutant of *Salmonella typhimurium*," *Vaccine*, 9:29–34 (1991).

Levine et al., "Attenuated Salmonella as Live Oral Vaccines Against Typhoid Fever and as Live Vectors," *J. Biotech.*, 44:193–196 (1996).

Manoil et al., "TnphoA: A Transposon Probe for Protein Export Signals," *Proc. Natl. Acad. Sci., USA*, 82:8129–8133 (1985).

Miles et al., "The Estimation of the Bactericidal Power of the Blood," *J. Hygiene*, 38:732–749 (1938).

Miller et al., "Bacteriophage P22 as a Vehicle for Transducing Cosmid Gene Banks Between Smooth Strains of *Salmonella typhimurium*: Use in Identifying a Role for aroD in Attenuating Virulent Salmonella Strains," *Mol. Gen. Genet.*, 215:312–316 (1989).

Miller et al., "Isolation of Orally Attenuated *Salmonella typhimurium* Following TnphoA Mutagenesis," *Infect. Immun.*, 57(9):2758–2763 (1989).

Miller et al., "A Two–Component Regulatory System (phoP phoQ) Controls *Salmonella typhimurium* Virulence," *Proc. Natl. Acad. Sci., USA*, 86:5054–5058 (1989).

Miller et al., "A Novel Suicide Vector and Its Use in Construction of Insertion Mutations: Osmoregulation of Outer Membrane Proteins and Virulence Determinants in *Vibrio cholerae* Requires toxR," *J. Bact.*, 170(6):2575–2583 (1988).

Oxer et al., "High Level Heterologous Expression in *E.coli* Using the Anaerobically–Activated nirB Promoter," *Nucl. Acids Res.*, 19(11):2889–2892 (1991).

Pickard et al., "Characterization of Defined ompR Mutants of *Salmonella typhi*: ompR is Involved in the Regulation of Vi Polysaccharide Expression," *Infect. Immun.*, 62(9):3984–3993 (1994).

Reed et al., "A Simple Method of Estimating Fifty Per Cent Endpoints," *Am. J. Hygiene*, 27(3):493–497 (1938).

Roberts et al., "A Mutant Pertussis Toxin Molecule That Lacks ADP–Ribosyltransferase Activity, PT–9K/129G, is an Effective Mucosal Adjuvant for Intranasally Delivered Proteins," *Infect. Immun.*, 63(6):2100–2108 (1995).

Stoker et al., "Versatile Low–Copy–Number Plasmid Vectors for Cloning in *Escherichia coli*," *Gene*, 18(3):335–341 (1982).

Strugnell et al., "Characterization of a *Salmonella typhimurium* aro Vaccine Strain Expressing the P.69 Antigen of *Bordetella pertussis*," *Infect. Immun.*, 60(10):3994–4002 (1992).

Tormo et al., "surA, an *Escherichia coli* Gene Essential for Survival in Stationary Phase," *J. Bact.*, 172(8):4339–4347 (1990).

Yura et al., "Systematic Sequencing of the *Escherichia coli* Genome: Analysis of the 0–2.4 min Region," *Nucl. Acids Res.*, 20(13):3305–3308 (1992).

\* cited by examiner

VACCINES CONTAINING ATTENUATED BACTERIA

This is a continuation of International Application No. PCT/GB98/03680, filed Dec. 10, 1998, the contents of which are hereby incorporated by referee.

BACKGROUND OF THE INVENTION

The principle behind vaccination is to induce an immune response in the host thus providing protection against subsequent challenge with a pathogen. This may be achieved by inoculation with a live attenuated strain of the pathogen (i.e. a strain having reduced virulence such that it does not cause the disease caused by the virulent pathogen).

Classically, live attenuated vaccine strains of bacteria and viruses have been selected using one of two different methodologies. Mutants have been created either by treatment of the organism using mutagenic chemical compounds or by repeated passage of the organism in vitro. However, use of either method gives rise to attenuated strains in which the mode of attenuation is unclear. These strains are particularly difficult to characterize in terms of possible reversion to the wild type strain as attenuation may reflect single (easily reversible) or multiple mutation events.

Using modem genetic techniques, it is now possible to construct genetically defined attenuated bacterial strains in which stable attenuating deletions can be created. A number of site directed mutants of *Salmonella* have been created using this type of technology (2, 5, 6, 12, 22, 35, 36, 37). Amongst the most comprehensively studied attenuating lesions are those in which mutations in the biosynthetic pathways have been created, rendering the bacteria auxotrophic (e.g. aro genes). Mutations in these genes were described as early as 1950 (1) as responsible for rendering Salmonella less virulent for mice. Several different auxotrophic mutations such as galE, aroA or purA have also been described previously (6, 12). Salmonella aroA mutants have now been well characterised and have been shown to be excellent live vaccines against salmonellosis in several animal species. In addition, in order to reduce the chances of a reversion to virulence by a recombination event mutations have now been introduced into two independent genes such as aroA/purA and aroA/aroC Identical mutations in host adapted strains of Salmonella such as *S. typhi* (man) and *S. dublin* (cattle) has also resulted in the creation of a number of single dose vaccines which have proved successful in clinical (11, 17) and field trials (15).

In animal studies, attenuated *S. typhimurium* has been used as a vehicle for the delivery of heterologous antigens to the immune system (3, 8, 32). This raises the potential of the development of multivalent vaccines for use in man (9).

SUMMARY OF THE INVENTION

The original aim of the work that led to the invention was the identification of novel genes that are involved in the virulence pathways of pathogenic bacteria, the identification and deletion of which may render the bacteria avirulent and suitable for use as vaccines. To identify attenuating lesions, random mutations were introduced into the chromosome of *S. typhimurium* using the transposon TnphoA (18). This transposon is unique in that it is engineered to identify proteins that are expressed in or at the bacterial outer membrane; such proteins may be those involved in interaction with and uptake by host tissues: By using the natural oral route of infection to screen these mutants, those with important, in vivo induced, attenuat lesions in genes were identified.

One such gene identified through this work is surA. The surA gene product is known to promote the folding of extracytoplasmic proteins. Accordingly, the invention provides a vaccine comprising a pharmaceutically acceptable carrier or diluent and a bacterium attenuated by a non-reverting mutation in a gene encoding a protein which promotes the folding of extracytoplasmic proteins. The vaccine has the ability to confer protection against a homologous wild type oral challenge with the virulent bacterium. In addition, the bacterium used in the vaccine can act as a carrier for heterologous antigens such as fragment C of tetanus toxin.

DETAILED DESCRIPTION OF THE INVENTION

Proteins that Promote the Folding of Extracytoplasmic Proteins

Periplasmic and outer membrane proteins are secreted across the cytoplasmic (inner) membrane in a mostly unfolded state, and they then fold after secretion. The folding often has enzymatic assistance to catalyse the formation of bonds necessary for the protein to reach its folded state. For example, the folding often requires the participation of enzymes that catalyse the formation of disulphide bonds or enzymes that catalyse the isomerisation of prolyl bonds (peptidyl-prolyl cis-tans isomerases or PPiases).

One known PPiase is SurA. The inventors have now shown that mutation of the surA gene causes attenuation of virulent bacteria and that the attenuated bacteria are useful as vaccines.

SurA was first described as being essential for the survival of *E.coli* in the stationary phase (33). It is a periplasmic protein. More recently, SurA has been described as belonging to a third, new family of PPiases (30), the parvulin family. Further studies have shown SurA to be involved in the correct folding of outer membrane proteins such as OmpA, OmpF, and LamB (16, 24, 29).

PPiases are divided into three families, the cyclophilins, FK506-binding proteins (FKBPs) and parvulins. Members of all three families have been found in *E.coli*. Apart from SurA, the parvulin family includes several proteins such as NifM, PrsA and PrtM.

Bacteria Useful in the Invention

The bacteria that are used to make the vaccines of the invention are generally those that infect via the oral route. The bacteria may be those that invade and grow within eukaryotic cells and/or colonise mucosal surfaces. The bacteria are generally Gram-negative.

The bacteria may be from the genera Salmonella, Escherichia, Vibrio, Haemophilus, Neisseria, Yersinia, Bordetella or Brucelia Examples of such bacteria are *Salmonella typhimurium* —the cause of salmonellosis in several animal species; *Salmonella typhi* —the cause of human typhoid; *Salmonella enteritidis* —a cause of food poisoning in humans; *Salmonella choleraesuis* —a cause of salmonellosis in pigs; *Salmonella dublin* —a cause of both a systemic and diarrhoel disease in cattle, especially of new-born calves; *Escherichia coli* —a cause of diarrhoea and food poisoning in humans; *Haemophilus influenzae* —a cause of meningitis; *Neisseria gonorrhoeae* —a cause of gonnorrhoeae; *Yersinia enterocolitica* —the cause of a spectrum of diseases in humans ranging from gastroenteritis to fatal septicemic disease; *Bordetella pertussis* —the cause of whooping cough; or *Brucella abortus* —a cause of abortion and infertility in cattle and a condition known as undulant fever in humans.

Salmonella bacteria are particularly useful in the invention. As well as being vaccines in their own right against infection by Salmonella, attenuated Salmonella can be used as carriers of heterologous antigens from other organisms to the immune system via the oral route. Salmonella are patent immunogens and are able to stimulate systemic and local cellular and antibody responses. Systems for driving expression of heterologous antigens in Salmonella in vivo are known; for example the nirB and hrrA promoters are known to be effective drivers of antigen expression in vivo.

The invention is also particularly applicable to *E.coli*, especially exterotoxigenic *E.coli* ("ETEC"). ETEC is a class of *E.coli* that cause diarrhoea. They colonise the proximal small intestine. A standard ETEC strain is ATCC H10407.

Infections of ETEC are the single most frequent cause of travellers diarrhoea, causing 3–9 million cases per year amongst visitors to developing countries. In endemic areas, ETEC infections are an important cause of dehydrating diarrhoea in infants and young children, resulting in 800,000 deaths a year in the under fives world-wide. In developing countries, the incidence of ETEC infections leading to clinical disease decreases with age, indicating that immunity to ETEC infection can be acquired. In contrast, naive adults from industrialized countries who visit endemic areas are highly susceptible to ETEC infections. However, with prolonged or repeated visits to endemic areas susceptibility to ETEC infections diminishes, suggesting that a live attenuated approach to ETEC vaccination may prove is successful.

Seq. Id. No. 1 shows the sequence of the surA open reading frame in *Salmonella typhimurium*, and Seq. Id. No. 2 shows the corresponding amino acid sequence. Seq. Id. No. 3 shows the sequence of the surA open reading frame in *E.coli*, and Seq. Id. N. 4 shows the corresponding amino acid sequence.

Second Mutations

The bacteria used in vaccines of the invention preferably contain a mutation in one or more genes in addition to the mutation in the gene encoding a protein which promotes folding of extracytoplasmic proteins. This is so that the risk of the bacterium reverting to the virulent state is minimised which is clearly important for the use of the bacterium as a human or animal vaccine. Although bacteria containing only a mutation in a protein which promotes folding of extracytoplasmic proteins are attenuated and the risk of reversion is small, it will generally be desirable to introduce at least one further mutation so as to reduce the risk of attenuation yet further A number of genes that are candidates for second and further mutations are known (see e.g. ref 39). These include the aro genes (35), the pur genes, the htrA gene (37), the ompR gene (36), the galE gene, the cya gene, the crp gene or the phoP gene. The aro gene may be aroA, aroC, aroD or aroE. The pur gene may be purA, purB, purE or purH. The use of aro mutants, especially double aro mutants, is preferred because such mutants have been shown to be particularly effective as vaccines. Suitable combinations of aro mutations are aroAaroC, aroAaroD and aroAaroE.

The Nature of the Mutation

The mutations introduced into the bacterial vaccine generally knock-out the function of the gene completely. This may be achieved either by abolishing synthesis of any polypeptide at all from the gene or by making a mutation that results in synthesis on non-functional polypeptide. In order to abolish synthesis of any polypeptide, either the entire gene or its 5'-end may be deleted. A deletion or insertion within the coding sequence of a gene may be used to create a gene that synthesises only non-functional polypeptide (e.g. polypeptide that contains only the N-terminal sequence of the wild-type protein). In the case of mutations in genes encoding proteins which promote the folding of extracytoplasmic proteins, the mutation generally abolishes the ability of the protein to promote such protein folding.

The mutations are non-reverting mutations. These are mutations that show essentially no reversion back to the wild-type when the bacterium is used as a vaccine. Such mutations include insertions and deletions. Insertions and deletions are preferably large, typically at least 10 nucleotides in length, for example from 10 to 600 nucleotides.

The bacterium used in the vaccine preferably contains only defined mutations, i.e. mutations which are characterised. It is clearly undesirable to use a bacterium which has uncharacterised mutations in its genome as a vaccine because there would be a risk that the uncharacterised mutations may confer properties on the bacterium that cause undesirable side-effects.

The attenuating mutations may be constructed by methods well known to those skilled in the art (see ref 31). One means for introducing non-reverting mutations into extracytoplasmic proteins is to use transposon TnphoA. This can be introduced into bacteria to generate enzymatically active protein fusions of alkaline phosphatase to extracytoplasmic proteins. The TnphoA transposon carries a gene encoding kanamycin resistance. Transductants are selected that are kanamycin resistant by growing colonies on an appropriate selection medium.

Alternative methods include cloning the DNA sequence of the wild-type gene into a vector, e.g. a plasmid or cosmid, and inserting a selectable marker into the cloned DNA sequence or deleting a part of the DNA sequence, resulting in its inactivation. A deletion may be introduced by, for example, cutting the DNA sequence using restriction enzymes that cut at two points in the coding sequence and ligating together the two ends in the remaining sequence. A plasmid carrying the inactivated DNA sequence can be transformed into the bacterium by known techniques. It is then possible by suitable selection to identify a mutant wherein the inactivated DNA sequence has recombined into the chromosome of the bacterium and the wild-type DNA sequence has been rendered non-functional in a process known as homologous recombination.

Expression of Heterologous Antigens

The attenuated bacterium used in the vaccine of the invention may be genetically engineered to express an antigen from another organism (a "heterologous antigen"), so that the attenuated bacterium acts as a carrier of the antigen from the other organism. In this way it is possible to create a vaccine which provides protection against the other organism. A multivalent vaccine may be produced which not only provides immunity against the virulent parent of the attenuated bacterium but also provides immunity against the other organism. Furthermore, the attenuated bacterium may be engineered to express more than one heterologous antigen, in which case the heterologous antigens may be from the same or different organisms.

The heterologous antigen may be a complete protein or a part of a protein containing an epitope. The antigen may be from another bacterium, a virus, a yeast or a fungus. More especially, the antigenic sequence may be from tetanus, hepatitis A, B or C virus, human rhinovirus such as type 2 or type 14, herpes simplex virus, poliovirus type 2 or 3, foot-and-mouth disease virus, influenza virus, coxsackie virus or *Chlamydia trachomatis*. Useful antigens include *E.coli* heat labile toxin B subunit (LT-B), *E.coli* K88 antigens, P.69 protein from *B. pertussis* and tetanus toxin fragment C.

The DNA encoding the heterologous antigen is expressed from a promoter that is active in vivo. Two good promoters are the nirB promoter (38, 40) and the htrA promoter (40).

A DNA construct comprising the promoter operably linked to DNA encoding the heterologous antigen may be made and transformed into the attenuated bacterium using conventional techniques. Transformants containing the DNA construct may be selected, for example be screening for a selectable marker on the construct. Bacteria containing the construct may be grown in vitro before being formulated for administration to the host for vaccination purposes.

Formulation of the Vaccine

The vaccine may be formulated using known techniques for formulating attenuated bacterial vaccines. The vaccine is advantageously presented for oral administration, for example in a lyophilised encapsulated form. Such capsules may be provided with an enteric coating comprising, for example, Eudragate "S" (Trade Mark), Eudragate "L" (Trade Mark), cellulose acetate, cellulose phthalate or hydroxypropylmethyl cellulose. These capsules may be used as such, or alternatively, the lyophilised material may be reconstituted prior to administration, e.g. as a suspension. Reconstitution is advantageously effected in a buffer at a suitable pH to ensure the viability of the bacteria. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramuscular administration.

The vaccine may be used in the vaccination of a host, particularly a human host but also an animal host An infection caused by a microorganism, especially a pathogen, may therefore be prevented by administering an effective dose of a vaccine prepared according to the invention. The dosage employed will be dependent on various factors including the size and weight of the host and the type of vaccine formulated. However, a dosage comprising the oral administration of from $10^7$ to $10^{11}$ bacteria per dose may be convenient for a 70kg adult human host.

EXAMPLES

The following Examples serve to illustrate the invention.

Figure 1:
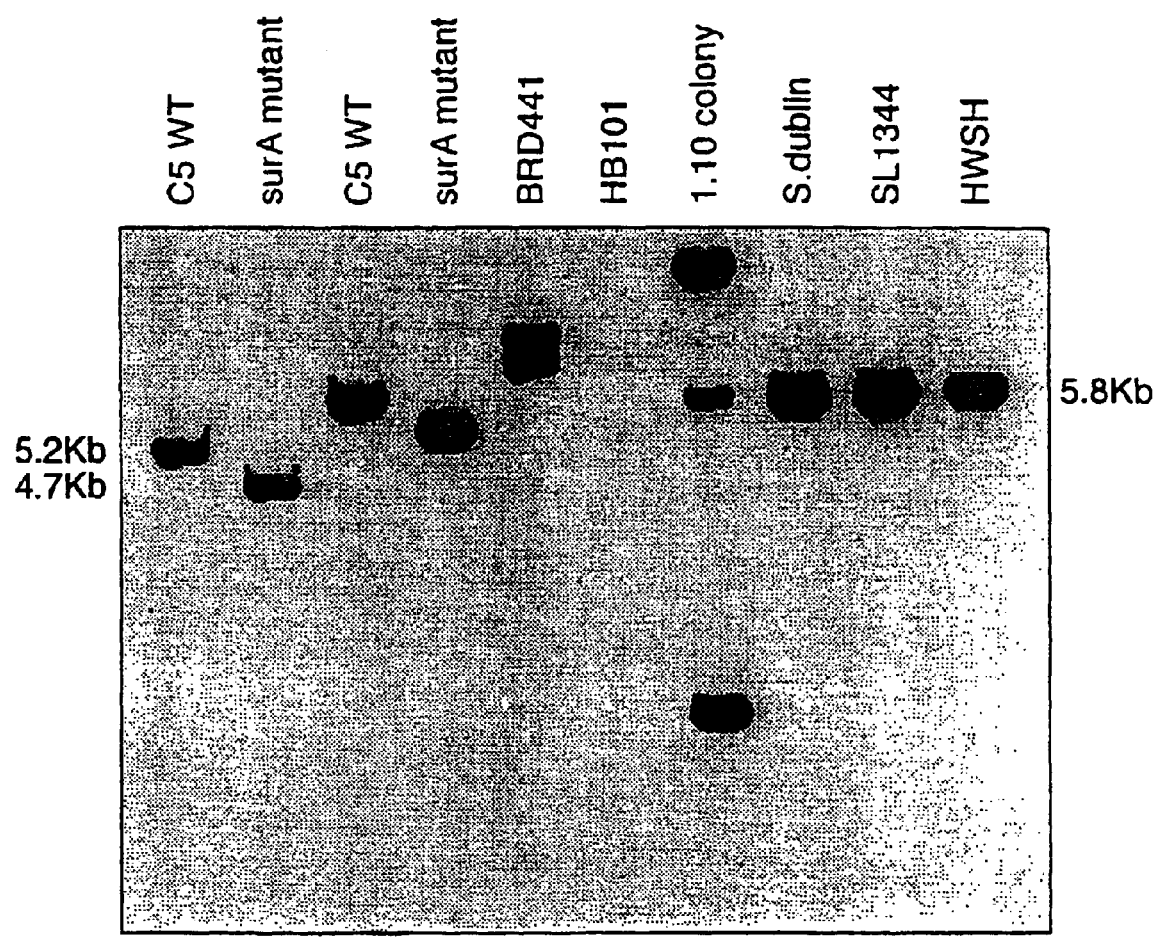
FIG. 1: Southern blot confining the defined deletion created within surA in the strain BRD1115. Lanes 1 and 2 have been restricted using the enzyme PstI, lanes 3–10 have been restricted with SalI. The filters have been probed using a 500 bp PCR product that contains a 500 bp fragment from the middle of the surA gene. Lanes 2 and 4 show hybridisation of this probe to a band 500 bp smaller than the corresponding wild type lanes 1 and 3. The transposon mutant BRD441 shows hybridisation to 2 bands since the enzyme SalI cuts the transposon into two. HB101 shows no hybridisation whilst the other wild type Salmonella strains show the same hybridisation as C5 when restricted with SalI.

FIG. 4: Schematic showing a plasmid map of pLG339/surA.

FIG. 5: Graph showing the survival of Balb/c mice following oral challenge with $\log_{10}8$ bacteria of the three stains C5, BRD1115 and K2.

Example 1

This Example shows the identification of mutations in surA as attenuating mutations, the construction of a defined surA mutation and the evaluation of a surA mutant as a vaccine (both against homologous challenge and as a carrier for heterologous antigens).

Materials and Methods 1.1 Bacteria, Bacteriophage, Plasmids and Growth Conditions The bacteria used in this study are listed in Table 1. Bacteria were routinely cultured on L-agar or in L-broth containing 100 μg/ml ampicillin or 50 μg/ml kanamycin where appropriate. The bacteriophage P22HT105/1int is a high frequency transducing bacteriophage obtained from Dr Tim Foster (Trinity College, Dublin). The plasmid pGEM-T (Promega Corporation, USA) is designed for direct cloning of PCR fragments and pBluescript°II SK+(Stratagene Ltd, Cambridge, U.K) is a general cloning vector. The other plasmids are described in the text 1.2 Purification of DNA and DNA Manipulation Techniques All DNA manipulation including Southern blotting were carried out as described by Sambrook et al (31). Restriction enzymes and T4 DNA ligase were purchased from Boehringer Mannheim (Lewes, UK) and used according to the manufacturers instructions. Chromosomal DNA preparation was prepared according to the method of Hull (13).

1.3 DNA Sequencing

Double stranded plasmid sequencing was carried out using the Sequenase kit (Trade Mark, United States Biochemical Corporation) according to the manufacturers' instructions. Labelling of the DNA was achieved using $^{35}S$-dATP (Amersham, UK) and fragments separated on an 8% acrylamide/bis-acrylamide gel containing 7M urea, for 2hours at 35 mA.

1.4 DNA Amplification by Polymerase Chain Reaction

Polymerase chain reactions (PCR) were carried out with Taq DNA polymerase using the GeneAmp kit (Trade Mark, Perkin Elmer Cetus, USA) according to the manufacturers' instructions. Oligonucleotides were purchased from the Molecular Medicine Unit, Kings College, London and the sequences are shown in Table 1. Mixtures of DNA and specific primers were subjected to multiple rounds of denaturation, annealing and extension in the presence of the enzyme Taq polymerase. 100 ng plasmid DNA and 1 mg chromosomal DNA were added to a mixture containing 5 $\mu$l 10×buffer (100 mM Tris-HCl, pH 8.3: 500 mM KCl; 15 mM Mg Cl$_2$, 0.01% gelatine(v/v)); 8 $\mu$l of deoxy-nucleotide mixture (1.25 mM each of deoxy-nucleotide triphosphate; dATP, dCTP, dGTP and dTTP); 1 $\mu$l of a 10 $\mu$M sense primer; 1 $\mu$l of a 10 $\mu$M anti-sense primer and 2.5 units Taq polymerase. This mixture is overlaid with 50 $\mu$l light mineral oil (Sigma) to prevent evaporation and the tubes incubated in an Omnigene Thermal Cycler (Trade Mark, Hybaid). Amplification of the DNA was performed using the following programme: 1 cycle of 95° C. for 5 minutes, 50° C. for 1.5 minutes, 74° C. for 2 minutes; 19 cycles of 95° C. for 1.5 minutes, 50° C for 2 minutes, 74° C. for 3 minutes; 10 cycles of 95° C. 2 minutes, 50° C. for 2 minutes, 74° C. for 7 minutes.

1.5 Transformation of Bacteria

1.5.1 Heat Shock

Bacteria are rendered competent to DNA uptake by the calcium chloride method. An overnight bacterial culture was used to seed a fresh 25 ml LB broth culture (a 1:100 dilution) which was grown aerobically with shaking until the cells reached mid-log growth phase (OD 650 nm=0.4 to 0.6). The cells were harvested by centrifugation at 3000×g for 10 minutes at 4° C. The supernatant was discarded and the pellet resuspended in 25 ml ice-cold 75 mM CaCl$_2$. The process was repeated and the cells incubated on ice for 30 minutes. The cells were pelleted by centrifugation at 3000×g for 10 minutes at 4° C. The cell pellet was resuspended in 1.2 ml ice-cold 75 mM CaCl$_2$ and stored on ice until needed. The cells were then competent to DNA uptake. A maximum of 20 $\mu$l of the ligation mix was added to 200 $\mu$l of the competent cells and the mixture stored on ice for 30 minutes. The cells were then subjected to heat shock by incubation in a 42° C. waterbath for 2 minutes. The cells were then transferred back to ice for a further 2 minutes. 1 ml of LB broth was added to the mixture and the cells incubated at 37° C. for at least 60 minutes to allow expression of the antibiotic marker on the plasmid. 100 $\mu$l aliquots of cells were plated onto LB agar plates containing the appropriate antibiotics and incubated overnight at 37° C.

1.5.2. Electroporation

Plasmid DNA was introduced into bacterial strains using electroporation. Mid-log phase growth cultures were generated as for the heat-shock method and the cells pelleted by centrifugation at 3000×g for 10 minutes at 4° C. The cell pellet was washed twice with an equal volume of ice-cold 10% glycerol and pelleted as before. The cell pellet was resuspended in 300–500 $\mu$l ice-cold 10% glycerol. Approximately 100 ng plasmid (or 1 $\mu$g suicide vector) in a volume not greater than 6 $\mu$l sterile water was added to 60 $\mu$l competent cells in a prechilled electroporation cuvette on ice. The plasmid was electroporated into the bacteria using a Bio-Rad Gene Pulser (Trade Mark) with the following conditions 1.75 kV, 600 $\Omega$, 25 $\mu$F. 1 ml LB broth was then added to the contents of the electroporation cuvette and the mixture incubated at 37° C. for 90 minutes to allow the cells to recover. 100 $\mu$l aliquots of the electroporation mix were plated out onto selection media and incubated at 37° C. overnight.

1.6 P22 Transduction

Transduction experiments were carried out using the bacteriophage P22 HT105/1 int$^-$. Phage lysates were prepared using LB5010 as the donor strain. A 5 ml overnight culture of LB5010 was grown in L broth containing 0.2% glucose and galactose to increase the expression of phage receptors on the cell surface. Ten fold serial dilutions of the P2 stock were made in TMGS up to $10^{-8}$ (stock is approximately $10^{10}$pfu/ml). 10 $\mu$l of each dilution was added to 100 $\mu$l of the overnight stock of cells and incubated at 37° C. for 30–45 minutes to allow adsorbtion of the phage to the cells. 3mls of top agar was added to each incubation and spread onto L agar plates containing 100 $\mu$g/ml ampicillin. The plates were incubated at 37° C. for approximately 4–5 hours until plaques were visible. The dilution that gave almost confluent plaques after this length of time was the one chosen for harvesting. The plaques were harvested by scraping the top agar into 2 ml of phage buffer with a glass microscope slide. A few drops of chloroform were added and the phage stock stored at 4° C. until needed. The recipient strain C5 was grown during the day in L broth at 37° C. until late log/stationary phase. 1 $\mu$l, 5 $\mu$l, 10 $\mu$l, 20 $\mu$l, and 50 $\mu$l aliquots of the new phage stock were added to 100 $\mu$l aliquots of the recipient strain and incubated at 37° C. for 1 hour. The cells were then spread onto L agar ampicillin plates containing 5 mM EGTA (to prevent phage replication) and incubated at 37° C. overnight. Colonies were replated onto L agar ampicillin plates containing 5 mM EGTA three times to ensure that they were free from phage. The colonies no longer had a jagged appearance thus indicating an absence of phage.

1.7 In Vitro Analysis of Bacterial Strain

1.7.1. Agglutination with Antisera

Agglutination using anti-sera raised against the O antigen of Salmonella can be used as a rapid test not only for the integrity of the bacterial LPS but also as a diagnostic of the strain, e.g. anti-sera against the 04 and 05 antigens for *S.typhimurium*. These were obtained from Murex Diagnostics Ltd (Dartford U.K.). A sweep of colonies was harvested from the growth on a plate incubated overight, and resuspended in 100 $\mu$l PBS. This sample was mixed with a drop of antisera on a glass slide and the agglutination compared with a positive and negative sample.

1.7.2 HEp-2 Invasion Assay

The HEp2 cell line is an adherent epidermoid carcinoma derived from human larynx (ATCC CCL23). It can be cultured as a monolayer in Dulbecco's modified Eagle's medium with 10% FCS, glutamine and penicillin/streptomycin at 37° C. in the presence of 5% CO$_2$. Confluent cells were detached from the tissue culture flasks by the use of trypsin/EDTA. The cells were first washed in PBS to remove any serum that might affect the action of the trypsin. Trypsin/EDTA was then added to the monolayer and the cells incubated at 37° C. for 5 minutes. The cells were removed from the plastic by gentle tapping on the edge of the flask. The trypsin was neutralised with 1.5 volumes of DMEM. Cells are collected by centrifugation at 1000×g for 5 minutes. The supernatant was removed and the cell pellet resuspended in DMEM. The cell pellet was counted and the concentration adjusted to give 2×10$^5$ cells per ml.

1 ml of the cell suspension was added to one well of a 24 well tissue culture plate (Costar 3524), three wells for each bacterial strain being investigated. The cells were incubated overnight to form a confluent monolayer in the well. The cells were then washed 5 times with PBS to ensure removal of the antibiotics and 1 ml DMEM added (without any antibiotics). 1×10$^7$ bacteria were added to each well and incubated at 37° C. for 3 hours. The cells were washed 3 times with PBS to remove any extracellular bacteria. 1 ml of DMEM containing 100 μg/m gentamycin was added and the cells incubated for a further 1 hour. The cells were washed 5 times with PBS. The cells were lysed by the addition of 1 ml of 0.1% Triton-X-100 at 37° C. for 15 minutes. The cells were further lysed by agitation with a blue pipette tip and the lysate transferred to a 1.5 ml centrifuge tube. The viable bacteria that had invaded the cells were counted using the Miles-Misra drop test method (19).

1.8. In Vivo Analysis of Bacterial Strains 1.8.1. Preparation of Live Bacteria for Immunisation of Mice.

A vial of the appropriate strain was thawed from liquid nitrogen and used to inoculate a 250 ml culture of LB broth containing antibiotic where appropriate. The culture was grown overnight at 37° C. without shaking. The bacteria were harvested by centrifugation at 3000×g for 10 minutes and washed once in sterile PBS. The bacteria were harvested again by centrifugation and resuspended in 5 ml sterile PBS. The concentration of bacteria was estimated by optical density at 650 nm using a standard growth curve for that strain. Based on this estimate the cell concentration was adjusted with PBS to that required for immunisation. A viable count was prepared of each inoculum to give an accurate number of colony forming units per ml (cfu/ml) administered to each animal.

1.8.2. Oral Immunisation of Mice with Live Bacteria.

The mice were lightly anaesthetised with a mixture of halothane and oxygen and the bacteria administered by gavage in 0.2 ml volumes using a gavage needle attached to a 1 ml syringe.

1.8.3. Intravenous (i.v.) Immunisation of Mice with Live Bacteria.

Mice were placed in a warm chamber and 0.2 ml volumes injected into a tail vein of each mouse using a 27 gauge needle.

1.8.4. Enumeration of Viable Bacteria in Mouse Organs.

Groups of four or five mice were sacrificed up to 7 weeks post oral immunisation with three bacterial strains. Spleens, livers, mesenteric lymph nodes and Peyer's patches were removed and homogenised in 10 ml sterile PBS using a stomacher (Colworth, U.K). Dilutions of these homogenates were plated out in LB agar with kanamycin if required and incubated overnight at 37° C. The number of viable bacteria present in each homogenate was then calculated from the dilution.

1.9. Determination of Antibody Titres Against Fragment C.

Serum antibody responses against fragment C were measured by enzyme linked immunosorbant assay (ELISA) as previously described (28) using 96 well EIA/RIA plates (Costar 3590). Absorbance values were read at $A_{490}$ and plotted against dilutions (data not shown). A normal mouse serum control was added to each ELISA plate and used to define the background level response.

1.10 Tetanus Toxin Challenge

Mice were challenged with 0.05 μg (50×50% lethal doses) of purified tetanus toxin as previously described (7), and fatalities recorded for 4 days.

Results 2.1 Cloning and Mapping of TnphoA Insertion Sites

A number of *S.typhimurium* TnphoA insertion mutants were previously identified as being attenuated when administered orally to BALB/c mice. In addition some of these mutants also exhibited a reduced ability to invade the cultured epithelial cell line HEp-2. To identify the genes that had been disrupted by the TnphoA insertion, genomic DNA was digested using Sau3A and cosmid banks prepared from each strain. These banks were screened using TnphoA probes and cosmids exhibiting homology with the 3' and 5' probes were examined. Fragments from these cosmids were cloned into the vector pBluescript°II SK+. The nucleotide sequence surrounding these insertion sites was determined and the genes identified. Two insertions were found to be within the htrA gene (14), one in the osmZ gene (10) and one in the surA gene.

The surA gene open reading frame of *Salmonella typhimurium* shown in Seq Id No. 1 is 1281 bases long, encoding a protein of some 427 amino acids with a molecular weight of 47.2Kd. This protein is virtually identical to that found in *E.coli* (34), and is described as being essential for survival in long term culture (33). The surA gene contains a leader peptidase cleavage site indicating that this is a transported protein. It has now been described as belonging to a peptidyl prolyl isomerase family, with a function to aid the correct folding of outer membrane proteins (16, 24, 29).

2.2 Introduction of a Defined Deletion into the SurA Gene.

Restriction analysis and DNA sequencing of the surA gene revealed the presence of single HpaI and SmaI restriction enzyme sites within the coding region of the gene which could be used to generate a deletion of 400 bases. The plasmid pGEM-T/212/213 was constructed containing a 3 Kb region encompassing the entire surA gene and flanking region. Digestion of the plasmid with the enzymes HpaI and SmaI, gel purification of the large 5.5 Kb fragment and re-ligation resulted in a plasmid containing a 419bp deletion within the surA gene. This plasmid was designated pGEM-T/ΔsurA.

2.3 Introduction of the SurA Deletion into the Chromosome of *S.typhimurium* C5.

The plasmid pGEM-T was digested with the two restriction enzymes SphI and SalI. The 2.6kb fragment containing the deleted surA gene was gel purified and ligated into the suicide replicon pGP704 that had previously been digested with the same enzymes. The suicide replicon pGP704 has been used previously to introduce deletions into the chromosome of *S.typhi* (4) and *S. typhimurium* (26) which lack the pir gene, the product of which is essential for the replication of pGP704. The ligation mix was used to transform the strain SY327, an *E. coli* strain that contains the pir gene, and a plasmid of the expected size identified by restriction analysis. This plasmid was designated pGP704/ΔsurA. Since suicide replicons cannot replicate in *S.typhimurium* the drug resistance marker is only expressed if there has been a single homologous recombination event, incorporating the plasmid into the bacterial chromosome.

The plasmid pGP704/ΔsurA was used to transform the semi-rough *S.typhimurium* strain LB5010 by the calcium chloride method. Three transformants were selected on agar containing ampicillin. These single crossovers were moved from this intermediate strain into the wild type C5 using P22 transduction (20). P22 lysates were prepared from the three transductants and introduced into C5. One ampicillin resistant colony was obtained from this process. This transformant was sub-cultured twice into L-broth containing no selection and grown for 48 hours. Serial dilutions of this culture were made and the $10^{-6}$ dilution was spread onto L-agar plates containing no selection. 500 colonies were streaked by hand on to duplicate plates, one containing agar, the other agar with ampicillin. One colony was found to be ampicillin sensitive indicating the loss of the drug resistance marker of the plasmid following a second homologous recombination event.

This potential surA mutant was confirmed as a *S.typhimurium* strain by agglutination with 04 and 05 antiserum.

The deletion was confirmed by PCR using the primers MGR92 and MGR93, giving a 1 kb product. The deletion was also confirmed cloning the PCR product into the vector pGEM-T to give the plasmid pGEM-T/92/93, and sequencing across the deletion using the primers MGR130 and 135. FIG. 1 shows the results of probing PstI and SalI digested genomic DNA from C5 and the surA mutant strain with a PCR product obtained from the wild type C5. The band seen in the surA mutant track is approximately 400 bases smaller than that seen in the wild type. This deleted strain was designated BRD1115.

2.4 Characterisation of the Strain BRD115

2.4.1 In Vitro Analysis of the Invasion of Cultured Epithelial Cells

The strain BRD1115 was tested for its ability to invade the cultured epithelial cell line HEp-2. The levels of invasion were found to be reduced by 80% in comparison to the wild type strain C5. The transposon mutant BRD441 showed a 90% reduction in invasion compared to C5.

2.4.2. Evaluation of the in Vivo Properties of BRD1115 in BALB/c Mice.

2.4.2.1. determination of Oral and i.v. LD50's

The oral and i.v. $LD_{50}$'s of BRD 1115, C5 and BRD441 were calculated using the mouse susceptible strain BALB/c. 5 mice per group were inoculated either orally or i.v. with doses ranging from $\log_{10}4$ to $\log_{10}10$ orally and $\log_{10}1$ to $\log_{10}5$ i.v. Deaths were recorded over 28 days and the $LD_{50}$'s calculated by the method of Reed and Meunch (27). BRD 1115 was determined to show nearly 5 logs of attenuation orally and 3.5 logs i.v compared to C5. BRD441 showed 4.5 logs attenuation orally and 1 log i.v The results are presented in Table 2.

Figure 2:
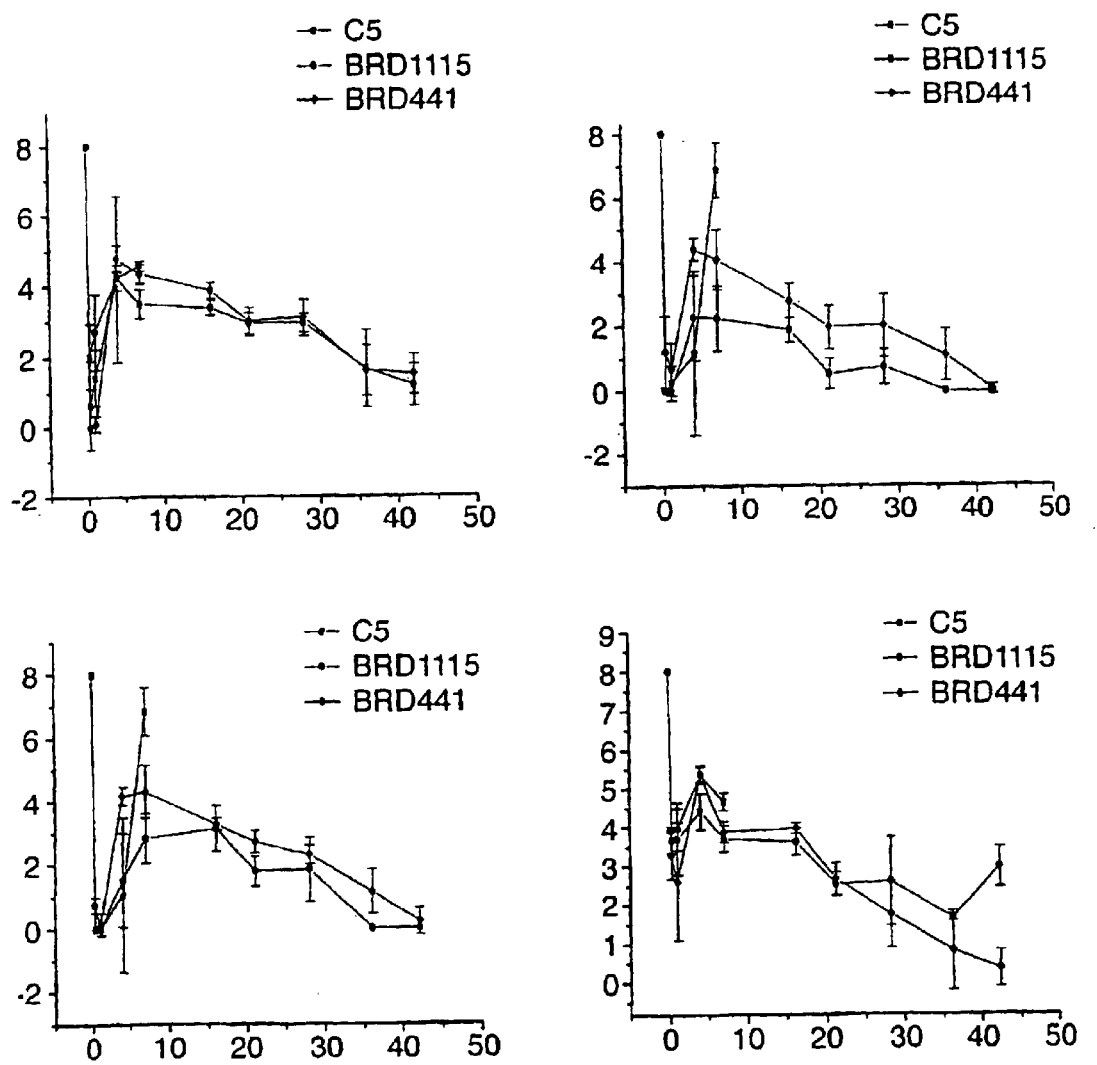
FIG. 2: This figure shows the colonisation and persistence of BRD1115, BRD441 and the wild type C5 in the mesenteric lymph nodes (top left graph), Peyer's patches (bottom right), spleens (bottom left) and livers (top right) in BALB/c mice following oral inoculation. The x-axis is time in days and the y-axis is $\log_{10}$ CFU/ml (CFU stands for colony forming units).

2.4.2.2. persistence of Strains in the Organs of BALB/c Mice Following Oral Inoculation Groups of 4 BALB/c mice were orally inoculated with $\log_{10}8$ organisms of the three strains. Mice were killed at days 0,1,4,7,10,16,21 and 28 and the organs examined for bacterial load. The wild type strain C5 colonised the spleen, liver, mesenteric lymph nodes and Peyer's patches in high numbers (>$\log_{10}4$ cfu/ml), eventually resulting in the death of the animals. BRD1115 and BRD 441 on the other hand persisted in the liver and spleens for more than 40 days in low numbers (<$\log_{10}2$ cfu/ml). These results are presented in FIG. 2.

2.5. Evaluation of BRD1115 as a Potential Vaccine Strain 2.5.1. BRD1115 Protects Against Homologous Challenge Groups of BALB/c mice were orally immunised with $\log_{10}8$ organisms of BRD1115 and challenged with the wild type strain C5 at 4 weeks and 10 weeks post inoculation. The mice were challenged with $\log_{10}4$ to $\log_{10}10$ organisms C5 and a new oral $LD_{50}$ calculated. The levels of protection are presented in Table 3, showing $\log_{10}4$ protection after 4 weeks and $\log_{10}5$ after 10 weeks.

2.5.2. BRD1115 as a Potential Carrier Strain for Heterologous Antigens

Two plasmids encoding the C fragment of tetanus toxin were introduced into two isolates of BRD1115 by electroporation. The plasmids are pTETnir15 (38) in which fragment C is under the control of the nirB promoter, and pTEThtrA in which fragment C is under the control of the htrA promoter. The plasmids were found to be maintained at levels greater than 90% in BRD1115 even when the selection pressure of ampicillin was removed from the growth medium. In vitro expression of fragment C was determined by Western blotting. The strains were cultured under both inducing (42° C. for BRD 1126 and anaerobiosis for BRD1127) and non-inducing conditions (37° C. for BRD 1126 and aerobiosis for BRD 1127). A higher level of expression was seen for both strains under inducing conditions with BRD 1127 showing higher levels of fragment C expression than BRD 1126.

Figure 3:
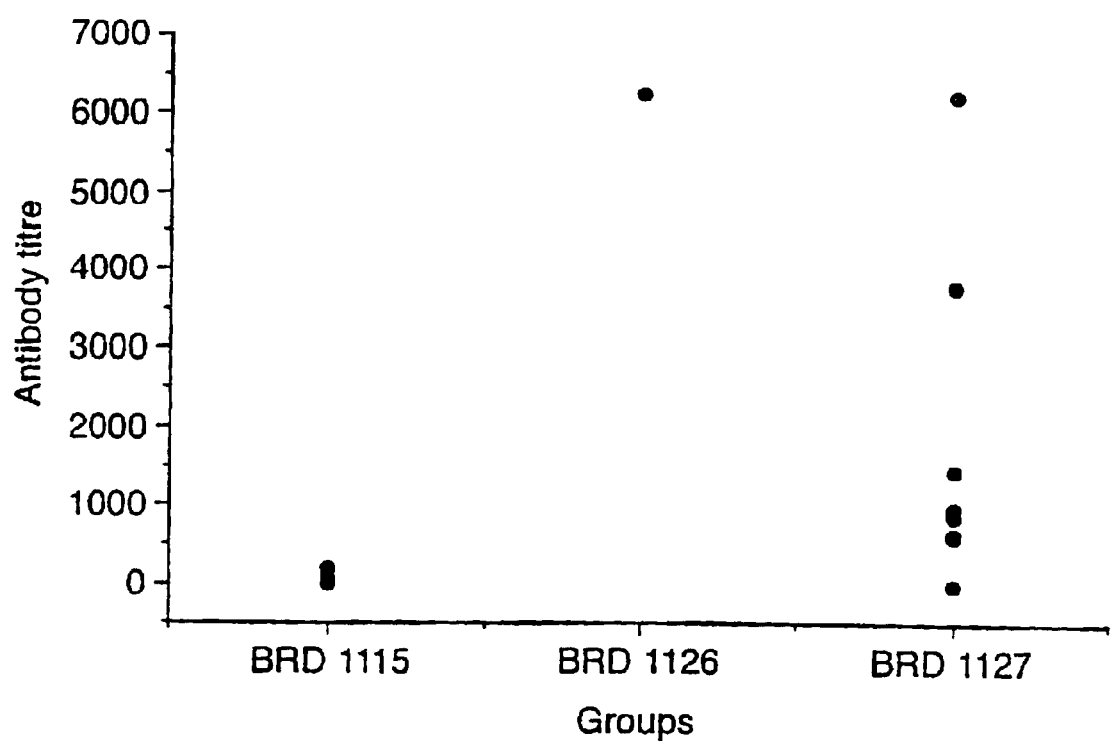
FIG. 3: Three strains were constructed to evaluate the ability of mutant Salmonella strains to deliver the heterologous antigen Fragment C in the mouse. BRD1115 is the parental strain. Two plasmids encoding the Fragment C gene of tetanus toxin under the control of either the htrA or nirB promoter were introduced into the strain BRD1115 to give the strains BRD1127 and 1126 respectively. Expression of fragment C was determined in vitro by Western blotting. These strains were then used in an in vivo experiment using BALB/c mice. Groups of 10 mice were immunised orally with $\log_{10}8$ organisms each of the 3 strains. Serum samples were taken weekly and analysed for total antibodies against tetanus toxin fragment C. The titres of anti-fragment C were determined as the highest sample dilution giving an absorbance value of 0.3 above normal mouse serum. The highest sample dilution tested was 1/6250. All mice immunised with BRD 1126 showed antibody titres higher than 6250.

Groups of 10 BALB/c mice were orally immunised with $\log_{10}8$ organisms and bled weekly. The titres of anti-fragment C antibodies present in the serum of each animal was determined by ELISA. The titres were determined as the reciprocal of the highest sample dilution giving an absorbance of 0.3 above normal mouse serum. The results are presented in FIG. 3.

Four weeks post immunisation the mice were challenged with $50LD_{50}$'s of tetanus toxin subcutaneously and the deaths noted over 4 days. The results are presented in Table 4, showing that 100% protection was given after immnunisation with BRD 1127 (fragment C under the control of the htrA promoter) and 60% protection after immunisation with BRD1126 (under nirB promoter). No naive mice survived the challenge.

Example 2

This Example confirms that the mutation in surA is responsible for the attenuation. This was determined by complementation of the deleted gene with an intact version of the gene expressed on a plasmid. The complemented strain was as virulent as the wild-type organism given orally to mice.

Figure 4:
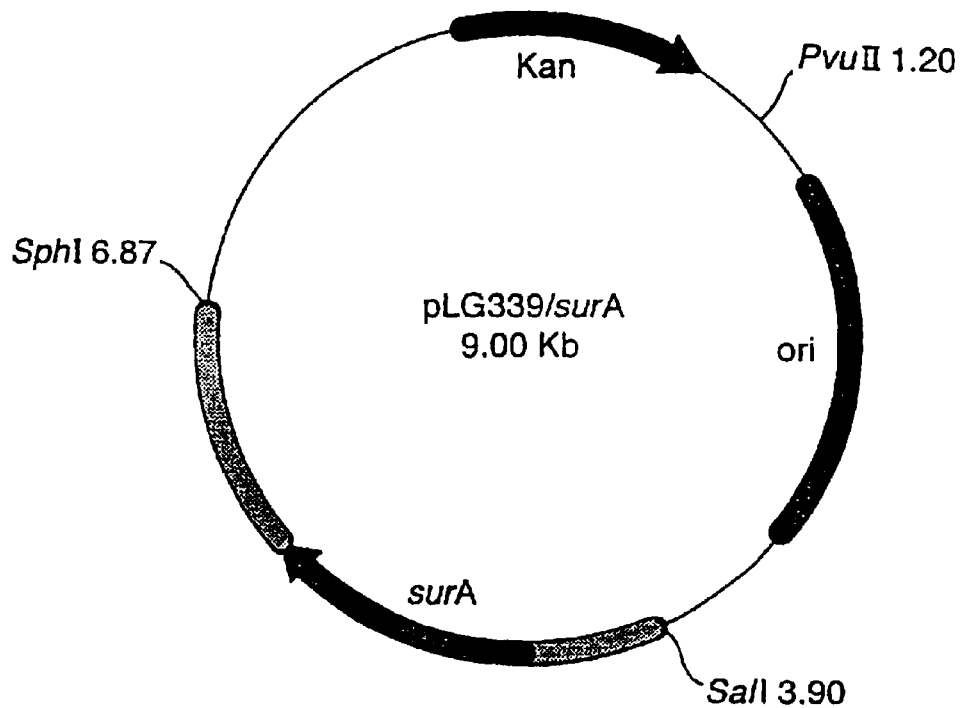

Materials and Methods 3.1 Construction of Plasmid Containing the Intact SurA Gene pLG339 (41) is a low copy number plasmid based on pSC105. A 3kb fragment of the plasmid pGEM-T/212/213 (section 2.2) containing the intact surA gene and flanking region was cloned into the SphI/SalI sites of the plasmid pLG339 to create the plasmid pLG339/surA. A schematic of this plasmid is shown in FIG. 4.

3.2 Introduction of the Plasmid pLG339/surA into Defined Mutant Strain BRD1115

The plasmid was electroporated into electrocompetent BRD 1115 as previously described in section 1.5.2. Transformants containing the plasmid were selected by plating the electroporation mix onto agar plates containing 15 µg/ml kanamycin. Plasmid DNA was recovered from a single colony of this transformation and checked for identity by restriction analysis. This strain was called K2.

3.3 Plasmid Stability Within the Strain K2.

The ability of the intact surA gene on the plasmid to complement the action of the deleted surA gene in the chromosome relies on the plasmid being retained within the bacterial stain. The plasmid contains the gene encoding resistance to the, antibiotic kanamycin. Culturing the strain in the presence of the antibiotic should ensure that the plasmid is retained. However it is important that the plasmid be retained in the absence of the antibiotic selection as antibiotic selection is not possible in vivo.

A single colony of the strain K2 was inoculated into duplicate 10 ml cultures of L broth with and without kanamycin. The cultures were grown with shaking at 37° C. for a total of 72 hours. Samples were taken at 30 and 48 hours post inoculation and serial dilutions plated onto L agar plates with and without kanamycin. The cultures were diluted 1/100 into Fresh L broth with and without kanamycin and cultured for a further 24 hours. Dilutions of the culture were again plated out onto L agar plates with and without kanamycin. Numbers of colony forming units (cfu) were recorded and are reported in Table 5.

3.4 Oral Immunisation of Mice with the Strain K2.

The strain K2 was grown as described in 1.8 and used to challenge orally groups of 5 Balb/c mice (as previously described) with a dose range from $10^4$ to $10^{10}$ dose. Deaths were recorded over 28 days and the $LD_{50}5$ so calculated according to the method of Reed and Meunch (described in 2.3.2).

Results

4.1 Strain

The plasmid pLG339/surA was recovered from the strain K2 and digested with the two enzymes SphI and SalI. Separation of the resultant bands by agarose gel electrophoresis revealed the correct sized bands of 6.2 and 3 kb.

4.2 Plasmid Stability

The presence of the plasmid pLG339/surA was investigated in the strain K2. The results show that in the absence of antibiotics the plasmid is retained by the bacteria. In these studies, at least 82% of the bacteria retain the plasmid when grown without antibiotics. This suggests that this plasmid should be maintained when the bacteria are used to infect mice.

4.3 Complementation Data

Groups of 5 Balb/c mice were orally challenged with various doses of the putative complemented strain K2. The oral $LD_{50}$ of the complemented strain K2 was calculated to be $\log_{10}4.35$ compared to that of $\log_{10}4.17$ for the parental strain C5.

Figure 5:
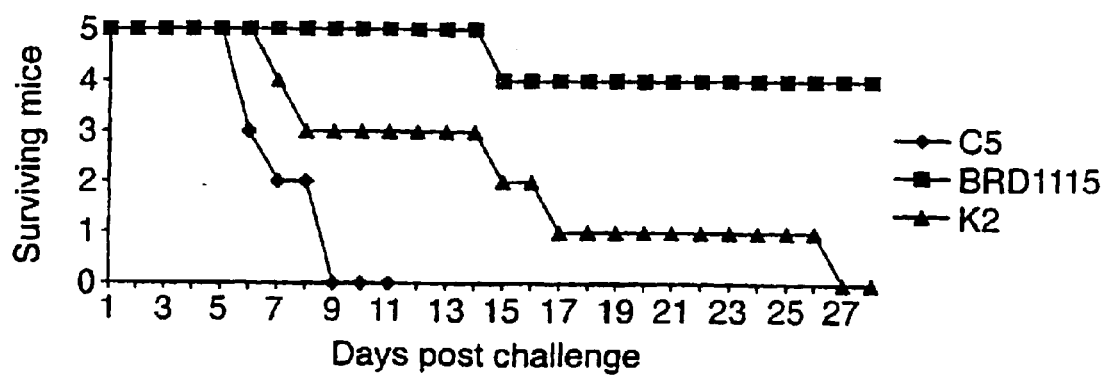

Deaths of the mice within the group of mice challenged with $\log_{10}8$ bacteria of the three strains C5, BRD1115 and K2 are represented in FIG. 5. Although the surA gene expressed from the plasmid appears to complement the defined mutation in vivo, the apparent delay in the time to death (when compared to the wild type parent strain) suggests the level of surA expression may be reduced in the strain K2.

Tables

TABLE 1

Bacterial strains, plasmids and oligonucleotide primers used in this study

| | Properties | Source or ref |
| --- | --- | --- |
| Bacterial strains | | |
| *E. coli* | | |
| SY327 | λpir lysogen | Miller V. L. (23) |
| *S. typhimurium* | | |
| LB5010 | semi-rough | the inventor laboratory |
| C5 | wild type | C. Hormaeche, Cambridge, U.K. |
| BRD441 | TnphoA mutant, kan$^R$ | Miller I (21) |
| BRD 1115 | | this study |
| BRD 1126 | amp$^R$ | Oxer M. D. (25) |
| BRD 1127 | amp$^R$ | in press |
| Plasmids | | |
| pBluescript$^5$II SK+ | amp$^R$ | Stratagene Ltd |
| pGEM-T | amp$^R$ | Promega Corp. |
| pGP704 | amp$^R$ | Miller V. L. (23) |
| pGEM-T/212/213 | amp$^R$ | this study |
| pGEM-T/ΔsurA | amp$^R$ | this study |
| pGP704/ΔsurA | amp$^R$ | this study |
| pGEM-T/92/93 | amp$^R$ | this study |
| pTETnir15 | amp$^R$ | Oxer M. D. (25) |
| pTEThtrA | amp$^R$ | in press |

TABLE 1-continued

Bacterial strains, plasmids and oligonucleotide primers used in this study

| | Properties | Source or ref |
| --- | --- | --- |
| Oligo Primers | | |
| MGR 92 | TCGGCACGCAAGAAATGT | Kings College, London |
| MGR 93 | AGACGACCAGTTCAATCG | Kings College, London |
| MGR 130 | CGATGGGCTGAACTATTC | Kings College, London |
| MGR 135 | TATGCAGCTTCGTTAGCG | Kings College, London |

TABLE 2

The oral and i.v. $LD_{50}$'s of the three strains C5, BRD 441 and BRD 1115 were determined in BALB/c mice. Groups of 5 mice were immunised with doses ranging from $\log_{10}4$ to $\log_{10}10$ cfu of the strains BRD 441 and BRD 1115, and doses $\log_{10}1$ to $\log_{10}5$ of the strain C5. The results are presented in the following table.

| Strain | oral $LD_{50}$ ($\log_{10}$ cfu) | i.v. $LD_{50}$ ($\log_{10}$ cfu) |
| --- | --- | --- |
| C5 | 4.16 | <1.87 |
| BRD 441 | 8.62 | 2.46 |
| BRD 1115 | 8.98 | 5.22 |

TABLE 3

The ability of the defined surA mutant strain to confer protection against homologous challenge with the wild type strain C5 was determined. Groups of 5 BALB/c mice were orally immunised with $\log_{10}8$ organisms of the strain BRD 1115 then challenged with $\log_{10}4$ to $\log_{10}10$ of the mouse virulent strain C5 either 4 or 10 weeks post inoculation. The new $LD_{50}$ was then calculated and the results presented in the table below.

| Immunising strain | oral $LD_{50}$ of C5 | | protection (no of $LD_{50}$'s) |
| --- | --- | --- | --- |
| | 4 weeks post immunisation | 10 weeks post immunisation | |
| BRD 1115 | 8.58 | | ~3800 |
| none | 4.74 | | |
| BRD 1115 | | 9.51 | ~4800 |
| none | | 4.68 | |

TABLE 4

Three groups of 10 mice were immunised with the strains BRD 1115, BRD 1126 and BRD 1127 and then challenged 4 weeks post immunisation with 50 $LD_{50}$ doses of tetanus toxin subcutaneously. Deaths were noted over 4 days. The numbers of mice surviving the challenge are presented in the table below.

| Strain | Survivors after challenge |
| --- | --- |
| BRD 1115 | 0/10 |
| BRD 1126 (nirB) | 6/10 |
| BRD 1127 (htrA) | 10/10 |

TABLE 5

The numbers of bacteria (cfu) present in the cultures of the complemented strain K2 following culture in L broth with and without the antibiotic kanamycin were calculated. The cultures were then plated onto L agar with and without kanamycin to show presence of the plasmid pLG339/surA. The results are presented as a total number and also the kanamycin resistant colonies as a percentage of the total bacteria present.

| Kanamycin in broth | Kanamycin in agar | 30 hours (%) | 48 hours (%) | 72 hours (%) |
|---|---|---|---|---|
| ++ | ++ | $4.75 \times 10^7$ (95%) | $6 \times 10^7$ (71%) | $8.25 \times 10^7$ (82.5%) |
| ++ | -- | $5 \times 10^7$ | $8.5 \times 10^7$ | $10 \times 10^7$ |
| -- | ++ | $5.25 \times 10^7$ (124%) | $9.5 \times 10^7$ (111%) | $6 \times 10^7$ (89%) |
| -- | -- | $4.25 \times 10^7$ | $8.5 \times 10^7$ | $6.75 \times 10^7$ |

References

1. Bacon, G. A., Burrows, T. W. and Yates, M. (1950) Br. J. Exp. Pathol. ., 31, 714–24.
2. Chatfield, S. N., Charles, I. G., Makoff, A. J. et. al. (1992a) Biotech, 10, 888–892.
3. Chatfield, S. N. Strahan,K., Pickard, D., Charles, I. G., Hormaeche, C. E. and Dougan, G. (1992b) Microbiol. Pathog., 12, 145–151.
4. Chatfield, S. N. Fairweather, N., Charles, I., Pickard, D., Levine, M. Hone, D., Posanda, M., Strugnell, R. A. and Dougan G. (1992) Vaccine, 10, 53–60.
5. Curtiss III, R. and Kelly, S. M. (1987) Infect. Immun. 55, 3035–3043.
6. Dougan, G. Chatfield, S., Pickard, D., Bester, J., O'Callaghan, D. and Maskell, D. (1988) J. Inf. Dis, 158,1329–1335.
7. Fairweather N. F., Lyness V. A., and Maskell D. J., (1987) Infect. Immun. 55, 2541–2545
8. Fairweather, N. F., Chatfield, S. N. Makoff, A. J. et. al. (1990) Infect. Immun., 58, 1323–1329.
9. Gomaz-Duarte, O. G., Galen, J. Chatfield, et. al. (1995) Vaccine, 13:1596–1602.
10. Harrison J. A., Pickard D., Higgins C. F., Khan A., Chatfield S., Ali T., Dorman C. J. Hormaeche C., and Dougan G., (1994) Mol. Micro., 13, 133–140
11. Hohmann, E. L., Oletta, C. A., Killeen, K. P. and Miller, S. I. (1996) Vaccine 14, 19–24.
12. Hone, D., Morona, R., Attridge, S. and Hackett, J. (1987) J. Infect Dis., 156, 167–1
13. Hull R. A. Gill R. E. Hsu P., Minshew B. H., and Falkow S., (1981) Infect. Immun. 33, 933–938
14. Johnson K., Charles I., Dougan G., Pickard D., O'Gaora P., Costa G., Ali T., Miller I., and Hormaeche C. (1991) Mol. Micro., 5, 401–407
15. Jones, P. W., Dougan, G. Haywood, C., MacKensie, N., Collins, P. and Chatfield, S. N. (1991) Vaccine 9, 29–36.
16. Lazar S. W., and Kolter R., (1 996) J.Bact. 178, 1770–1773
17. Levine, M. M., Galen, J., Barry, E., et al (1995) J. Biotech., 44, 193–196.
18. Manoil, C. and Beckwith, J. (1985) Proc. Natl. Acad. Sci., USA 82, 8129–8133.
19. Miles, A. A., Misra, S. S. and Irwin, J. (1938) J. Hygiene, 38, 732–749.
20. Miller I., Chatfield S., Dougan G., Desilva L., Joysey H. S., and Hormaeche C., (1989a) Mol. Gen. Genet., 215, 312–316
21. Miller, I., Maskell, D., Hormaeche, C., Pickard, D. and Dougan, G. (1989b) Infect. Immun. 57, 2758–2763.
22. Miller, S. I., Kukral, A. M. and Mekalanos, J. J. (1989). Proc. Natl. Acad. Sci., USA 86, 5054–5058.
23. Miller V. L., and Mekalanos J. J. (1988) J.Bact. 170,2575
24. Missiakis D., Betton J. M., and Raina S., (1996) Mol. Micro., 21, 871–884
25. Oxer, M. D., Bentley, C. M., Doyle, J. G. Peakman, T. C., Charles, I. G. and Makoff, A. J. (1991) Nucl. Acids Res. .19, 2889–2892.
26. Pickard, D., Li., J. L., Roberts, M., Maskell, D., Hone, D., Levine, M., Dougan, G. and Chatfield, S. (1994), 62, 3984–3993.
27. Reed L. J., and Meunch H., (1938) Am. J. Hygiene 27, 493–497
28. Roberts M., Bacon A., Rappuoli R., Pizza M., Cropley I., Douce G., Dougan G., 27 Marinaro M., McGhee J., and Chatfield S., (1995) Infect. Immun. 63, 2100–2108
29. Rouviere P. E., and Gross C. A., (1996) Genes Dev., 10, 3170–3182
30. Rudd K. E., Sofia H. J., Koonin E. V., Plunkett III G., Lazar S., and Rouviere P. E. (1995) TIBS 20, 12–14.
31. Sambrook J., Fritsch E. F., and Maniatis T., (1989) Molecular Cloning. A Laboratory Manual. Cold Spring Harbor Laboratory, Cold Spring Harbor, N.Y., USA
32. Strugnell, R. A. Dougan, G., Chatfied, S. N. et. al. (1992) Infect. Immun., 60, 3994–4002.
33. Tormo A., Almiron M., and Kolter R., (1990) J.Bact. 172, 4339–4347
34. Yura T., Mori H., Nagai H., Nagata T., Ishihama A., Fujita N., Isono K., Mizobuchi K., and Nakata A.(1992) Nucl. Acids Res., 20, 3305–3308
35. EP-B-0322237 (Dougan et al)
36. EP-B-0400958 (Dougan et al)
37. EP-B-0524205 (Dougan et al)
38. WO 92/15689 (Charles et al)
39. Chatfield, S. N., Strugnell. R. A. and Dougan, G (1989) Vaccine, 7, 495–498
40. Everest, P., Allen, J., Papakonstantinopoulou, A., Mastroeni, P., Roberts, M. and Dougan, G. (1995) FEMS Microbiol. Letts., 126, 97–101
41. Stoker N. G., Fairweather N. F., and Spratt B. G. (1982) Gene 18(3) 335–341

What is claimed is:

1. A composition which invokes an immune response to a pathogenic bacterium comprising an immunogenically effective amount of a pathogenic bacterium attenuated by a non-reverting, defined mutation in the surA gene and a pharmaceutically acceptable carrier or diluent.

2. The composition according to claim 1 wherein the bacterium is further attenuated by a non-reverting, defined mutation in a second gene.

3. The composition according to claim 2 wherein the second gene is selected from an aro gene, pur gene, htrA gene, ompR gene, galE gene, cya gene, crp gene or phoP gene.

4. The composition according to claim 3 wherein the aro gene is selected from aroA, aroC, aroD, or aroE.

5. The composition according to claim 1 wherein the bacterium has no uncharacterised mutations in the genome thereof.

6. The composition according to claim 1 wherein the bacterium is a bacterium that infects via the oral route.

7. The composition according to claim 1 wherein the bacterium is selected from the genera *Salmonella, Escherichia, Vibrio, Haemophilus, Neisseria, Yersinia, Bordetella* or *Brucella*.

8. The composition according to claim 7 wherein the bacterium is selected from *Salmonella typhimurium, Salmonella typhi, Salmonella enteritidis, Salmonella choleraesuis, Salmonella dublin, Escherichia coli, Haemophilus influenzae, Neisseria gonorrhoeae, Yersinia enterocolitica, Bordetella pertussis* or *Brucella abortus*.

9. The composition according to claim 1 wherein the bacterium is genetically engineered to express an antigen from another organism.

10. The composition according to claim 9 wherein the antigen is fragment C of tetanus toxin.

11. The composition according to claim 9 wherein expression of the antigen is driven by the nirB promoter or the htrA promoter.

12. The composition according to claim 10 wherein expression of the antigen is driven by the nirB promoter or the htrA promoter.

13. The composition according to claim 1 wherein the mutation is a deletion mutation.

14. The composition according to claim 1 wherein the mutation is an insertion mutation.

15. A method of invoking an immune response in a host to a pathogenic bacterium, which method comprises administering to the host an immunogenically effective amount of a pathogenic bacterium attenuated by a non-reverting, defined mutation in the surA gene.

16. The method according to claim 15 wherein the bacterium is further attenuated by a non-reverting, defined mutation in a second gene.

17. The method according to claim 16 wherein the second gene is selected from an aro gene, pur gene, htrA gene, ompR gene, galE gene, cya gene, crp gene or phoP gene.

18. The method according to claim 17 wherein the aro gene is selected from aroA, aroC, aroD, or aroE.

19. The method according to claim 15 wherein the bacterium has n uncharacterised mutations in the genome thereof.

20. The method according to claim 15 wherein the bacterium is a bacterium that infects via the oral route.

21. The method according to claim 15 wherein the bacterium is selected from the genera *Salmonella, Escherichia, Vibrio, Haemophilus, Neisseria, Yersinia, Bordetella* or *Brucella*.

22. The method according to claim 21 wherein the bacterium is selected from *Salmonella typhimurium, Salmonella typhi, Salmonella enteritidis, Salmonella choleraesuis, Salmonella dublin, Escherichia coli, Haemophilus influenzae, Neissera gonorrhoeae, Yersinia enterocolitica, Bordetella pertussis* or *Brucella abortus*.

23. The method according to claim 15 wherein the bacterium is genetically engineered to express an antigen from another organism.

24. The method according to claim 23 wherein the antigen is fragment C of tetanus toxin.

25. The method according to claim 23 wherein expression of the antigen is driven by the nirB promoter or the htrA promoter.

26. The method according to claim 15 wherein the mutation is a deletion mutation.

27. The method according to claim 15 wherein the mutation is an insertion mutation.

* * * * *

SEQUENCE LISTING

<160> NUMBER OF SEQ ID NOS: 4

<210> SEQ ID NO 1
<211> LENGTH: 1287
<212> TYPE: DNA
<213> ORGANISM: Salmonella typhimurium

<400> SEQUENCE: 1

```
atgaagaact ggaaaacgct gcttctcggt atcgccatga tcgcgaatac cagtttcgct     60
gccccccagg tagtcgataa agtcgcagcc gtcgtcaata atggcgtcgt gctggaaagc    120
gacgttgatg gcttaatgca atcagtcaaa ctcaacgcgg gtcaggcagg tcagcagctt    180
ccggacgacg ccacgctgcg tcaccagatc ctggaacgtt tgattatgga tcaaattatc    240
ctgcagatgg gtcagaagat ggggggtgaag atcacggatg agcagttgga tcagccatca    300
gccaacatcg ccaaacaaaa caatatgacg atggatcaga tgcgcagccg tctggcttac    360
gatgggctga actattcaac ctaccgtaac cagattcgta agagatgat tatctctgaa    420
gtgcgcaaca atgaggttcg tcgccgtatc accgttttgc cgcaagaagt tgacgcgctg    480
gcaaaacaga ttggcaccca aaacgatgcc agcaccgagc tgaacctgag ccatatcctg    540
attgctctgc cggaaaaccc aacctccgag caggttaacg acgcgcagcg ccaggcggaa    600
agcattgttg aagaagcgcg taacggcgca gatttcggca aactggcgat tacctactct    660
gccgaccagc aggcgctaaa aggcggtcag atgggctggg gccgtatcca ggagctgccg    720
gggattttcg cccaggcgct gagcaccgcg aagaaaggcg acattgtcgg cccgattcgc    780
tccggcgtcg gcttccacat tctgaaagta aatgacctgc gcggtcagag ccagagtatc    840
tccgtgaccg aagttcacgc tcgtcacatt ctgcttaagc cgtcgccgat catgaacgat    900
cagcaggcgc gcctgaagct ggaagaaatc gcggctgaca ttaagagtgg taaaaccacc    960
tttgccgctg cggcgaaaga gtactctcag gacccgggct ccgctaacca gggcggtgat   1020
ttgggttggg ctacgccaga tattttcgac ccggcgttcc gcgacgcgct aacgaagctg   1080
cataaaggcc aaataagcgc gccggtacac tcctctttcg gctggcatct gatcgaattg   1140
ctggatacgc gtaaggtaga caaaaccgat gcggcgcaga aagatcgcgc ttatcgtatg   1200
ctgatgaacc gtaaattctc agaagaagcg gcgacctgga tgcaagaaca gcgcgccact   1260
tacgttaaga ttttgagtaa ctaatga                                       1287
```

<210> SEQ ID NO 2
<211> LENGTH: 427
<212> TYPE: PRT
<213> ORGANISM: Salmonella typhimurium

<400> SEQUENCE: 2

```
Met Lys Asn Trp Lys Thr Leu Leu Leu Gly Ile Ala Met Ile Ala Asn
 1               5                  10                  15

Thr Ser Phe Ala Ala Pro Gln Val Val Asp Lys Val Ala Ala Val Val
                20                  25                  30

Asn Asn Gly Val Val Leu Glu Ser Asp Val Asp Gly Leu Met Gln Ser
            35                  40                  45

Val Lys Leu Asn Ala Gly Gln Ala Gly Gln Gln Leu Pro Asp Asp Ala
        50                  55                  60

Thr Leu Arg His Gln Ile Leu Glu Arg Leu Ile Met Asp Gln Ile Ile
 65                  70                  75                  80
```

```
Leu Gln Met Gly Gln Lys Met Gly Val Lys Ile Thr Asp Glu Gln Leu
                85                  90                  95
Asp Gln Pro Ser Ala Asn Ile Ala Lys Gln Asn Asn Met Thr Met Asp
            100                 105                 110
Gln Met Arg Ser Arg Leu Ala Tyr Asp Gly Leu Asn Tyr Ser Thr Tyr
        115                 120                 125
Arg Asn Gln Ile Arg Lys Glu Met Ile Ile Ser Glu Val Arg Asn Asn
    130                 135                 140
Glu Val Arg Arg Arg Ile Thr Val Leu Pro Gln Glu Val Asp Ala Leu
145                 150                 155                 160
Ala Lys Gln Ile Gly Thr Gln Asn Asp Ala Ser Thr Glu Leu Asn Leu
                165                 170                 175
Ser His Ile Leu Ile Ala Leu Pro Glu Asn Pro Thr Ser Glu Gln Val
            180                 185                 190
Asn Asp Ala Gln Arg Gln Ala Glu Ser Ile Val Glu Glu Ala Arg Asn
        195                 200                 205
Gly Ala Asp Phe Gly Lys Leu Ala Ile Thr Tyr Ser Ala Asp Gln Gln
    210                 215                 220
Ala Leu Lys Gly Gly Gln Met Gly Trp Gly Arg Ile Gln Glu Leu Pro
225                 230                 235                 240
Gly Ile Phe Ala Gln Ala Leu Ser Thr Ala Lys Lys Gly Asp Ile Val
                245                 250                 255
Gly Pro Ile Arg Ser Gly Val Gly Phe His Ile Leu Lys Val Asn Asp
            260                 265                 270
Leu Arg Gly Gln Ser Gln Ser Ile Ser Val Thr Glu Val His Ala Arg
        275                 280                 285
His Ile Leu Leu Lys Pro Ser Pro Ile Met Asn Asp Gln Gln Ala Arg
    290                 295                 300
Leu Lys Leu Glu Glu Ile Ala Ala Asp Ile Lys Ser Gly Lys Thr Thr
305                 310                 315                 320
Phe Ala Ala Ala Ala Lys Glu Tyr Ser Gln Asp Pro Gly Ser Ala Asn
                325                 330                 335
Gln Gly Gly Asp Leu Gly Trp Ala Thr Pro Asp Ile Phe Asp Pro Ala
            340                 345                 350
Phe Arg Asp Ala Leu Thr Lys Leu His Lys Gly Gln Ile Ser Ala Pro
        355                 360                 365
Val His Ser Ser Phe Gly Trp His Leu Ile Glu Leu Leu Asp Thr Arg
    370                 375                 380
Lys Val Asp Lys Thr Asp Ala Ala Gln Lys Asp Arg Ala Tyr Arg Met
385                 390                 395                 400
Leu Met Asn Arg Lys Phe Ser Glu Glu Ala Ala Thr Trp Met Gln Glu
                405                 410                 415
Gln Arg Ala Thr Tyr Val Lys Ile Leu Ser Asn
            420                 425

<210> SEQ ID NO 3
<211> LENGTH: 1287
<212> TYPE: DNA
<213> ORGANISM: Escherichia coli

<400> SEQUENCE: 3
atgaagaact ggaaaacgct gcttctcggt atcgccatga tcgcgaatac cagtttcgct     60
gccccccagg tagtcgataa agtcgcagcc gtcgtcaata acggcgtcgt gctggaaagc    120
gacgttgatg gattaatgca gtcggtaaaa ctgaacgctg ctcaggcaag gcagcaactt    180
```

-continued

```
cctgatgacg cgacgctgcg ccaccaaatc atggaacgtt tgatcatgga tcaaatcatt       240
ctgcagatgg ggcagaaaat gggagtgaaa atctccgatg agcagctgga tcaggcgatt       300
gctaacatcg cgaaacagaa caacatgacg ctggatcaga tgcgcagccg tctggcttac       360
gatggactga actacaacac ctatcgtaac cagatccgca agagatgat tatctctgaa        420 gtgcgtaaca acgaggtgcg tcgtcgcatc accatcctgc cgcaggaagt cgaatccctg       480
gcgcagcagg tgggtaacca aaacgacgcc agcactgagc tgaacctgag ccacatcctg       540
atcccgctgc cggaaaaccc gacctctgat caggtgaacg aagcggaaag ccaggcgcgc       600
gccattgtcg atcaggcgcg taacggcgct gatttcggta agctggcgat tgctcattct       660
gccgaccagc aggcgctgaa cggcggccag atgggctggg ccgtattca ggagttgccc        720 gggatcttcg cccaggcatt aagcaccgcg aagaaaggcg acattgttgg cccgattcgt       780
tccggcgttg gcttccatat tctgaaagtt aacgacctgc gcggcgaaag caaaaatatc       840
tcggtgaccg aagttcatgc tcgccatatt ctgctgaaac cgtcgccgat catgactgac       900
gaacaggccc gtgtgaaact ggaacagatt gctgctgata tcgagagtgg taaaacgact       960
tttgctgccg caacgaaaga gttctctcag gatccagtct ctgctaacca gggcggcgat      1020
ctcggctggg ctacaccaga tattttcgat ccggccttcc gtgacgccct gactcgcctg      1080
aacaaaggtc aaatgagtgc accggttcac tcttcattcg gctggcattt aatcgaactg      1140
ctggatcccc gtaatgtcga taaaaccgac gctgcgcaga agatcgtgc ataccgcatg       1200 ctgatgaacc gtaagttctc ggaagaagca gcaagctgga tgcaggaaca acgtgccagc      1260
gcctacgtta aaatcctgag caactaa                                          1287
```

<210> SEQ ID NO 4
<211> LENGTH: 428
<212> TYPE: PRT
<213> ORGANISM: Escherichia coli

<400> SEQUENCE: 4

```
Met Lys Asn Trp Lys Thr Leu Leu Gly Ile Ala Met Ile Ala Asn
 1               5                  10                  15

Thr Ser Phe Ala Ala Pro Gln Val Val Asp Lys Val Ala Ala Val
                20                  25                  30

Asn Asn Gly Val Val Leu Glu Ser Asp Val Asp Gly Leu Met Gln Ser
             35                  40                  45

Val Lys Leu Asn Ala Ala Gln Ala Arg Gln Gln Leu Pro Asp Asp Ala
         50                  55                  60

Thr Leu Arg His Gln Ile Met Glu Arg Leu Ile Met Asp Gln Ile Ile
 65                  70                  75                  80

Leu Gln Met Gly Gln Lys Met Gly Val Lys Ile Ser Asp Glu Gln Leu
                 85                  90                  95

Asp Gln Ala Ile Ala Asn Ile Ala Lys Gln Asn Asn Met Thr Leu Asp
                100                 105                 110

Gln Met Arg Ser Arg Leu Ala Tyr Asp Gly Leu Asn Tyr Asn Thr Tyr
             115                 120                 125

Arg Asn Gln Ile Arg Lys Glu Met Ile Ile Ser Glu Val Arg Asn Asn
         130                 135                 140

Glu Val Arg Arg Arg Ile Thr Ile Leu Pro Gln Glu Val Glu Ser Leu
145                 150                 155                 160

Ala Gln Gln Val Gly Asn Gln Asn Asp Ala Ser Thr Glu Leu Asn Leu
                165                 170                 175
```

-continued

```
Ser His Ile Leu Ile Pro Leu Pro Glu Asn Pro Thr Ser Asp Gln Val
            180                 185                 190

Asn Glu Ala Glu Ser Gln Ala Arg Ala Ile Val Asp Gln Ala Arg Asn
        195                 200                 205

Gly Ala Asp Phe Gly Lys Leu Ala Ile Ala His Ser Ala Asp Gln Gln
        210                 215                 220

Ala Leu Asn Gly Gly Gln Met Gly Trp Gly Arg Ile Gln Glu Leu Pro
225                 230                 235                 240

Gly Ile Phe Ala Gln Ala Leu Ser Thr Ala Lys Lys Gly Asp Ile Val
                245                 250                 255

Gly Pro Ile Arg Ser Gly Val Gly Phe His Ile Leu Lys Val Asn Asp
                260                 265                 270

Leu Arg Gly Glu Ser Lys Asn Ile Ser Val Thr Glu Val His Ala Arg
            275                 280                 285

His Ile Leu Leu Lys Pro Ser Pro Ile Met Thr Asp Glu Gln Ala Arg
    290                 295                 300

Val Lys Leu Glu Gln Ile Ala Ala Asp Ile Glu Ser Gly Lys Thr Thr
305                 310                 315                 320

Phe Ala Ala Thr Lys Glu Phe Ser Gln Asp Pro Val Ser Ala Asn
                325                 330                 335

Gln Gly Gly Asp Leu Gly Trp Ala Thr Pro Asp Ile Phe Asp Pro Ala
                340                 345                 350

Phe Arg Asp Ala Leu Thr Arg Leu Asn Lys Gly Gln Met Ser Ala Pro
            355                 360                 365

Val His Ser Ser Phe Gly Trp His Leu Ile Glu Leu Leu Asp Thr Arg
    370                 375                 380

Asn Val Asp Lys Thr Asp Ala Ala Gln Lys Asp Arg Ala Tyr Arg Met
385                 390                 395                 400

Leu Met Asn Arg Lys Phe Ser Glu Glu Ala Ala Ser Trp Met Gln Glu
                405                 410                 415

Gln Arg Ala Ser Ala Tyr Val Lys Ile Leu Ser Asn
                420                 425
```